United States Patent [19]
Hamamoto et al.

[11] Patent Number: 5,720,862
[45] Date of Patent: Feb. 24, 1998

[54] SENSOR AND PRODUCTION METHOD OF AND MEASUREMENT METHOD USING THE SAME

[75] Inventors: Katsumi Hamamoto; Hisashi Okuda, both of Kyoto, Japan

[73] Assignee: Kyoto Daiichi Kagaku Co., Ltd., Kyoto-fu, Japan

[21] Appl. No.: 628,485

[22] Filed: Apr. 5, 1996

[30] Foreign Application Priority Data

Apr. 7, 1995 [JP] Japan .................................. 7-082332

[51] Int. Cl.$^6$ .................................................. G01N 27/26
[52] U.S. Cl. ................ 204/403; 204/415; 435/289.1; 435/817; 205/777.5; 205/778
[58] Field of Search ................................... 204/403, 415, 204/418; 435/817, 289.1; 205/777.5, 778

[56] References Cited

U.S. PATENT DOCUMENTS 5,264,103  11/1993  Yoshioka et al. ................ 204/403

FOREIGN PATENT DOCUMENTS

| 0502504 | 9/1992 | European Pat. Off. . |
|---|---|---|
| 0537761 | 4/1993 | European Pat. Off. . |
| 0636879 | 2/1995 | European Pat. Off. . |
| 53-004557 | 1/1983 | Japan . |
| 2062952 | 3/1990 | Japan . |
| 3-054447 | 3/1991 | Japan . |
| 4113262 | 4/1992 | Japan . |
| 5-079319 | 11/1993 | Japan . |
| 6-094672 | 4/1994 | Japan . |
| 2230865 | 10/1990 | United Kingdom . |

OTHER PUBLICATIONS

J.R. Mor and R. Guanaccia, "Assay of Glucose Using an Electrochemical Enzymatic Sensor" Anal. Biochem., vol. 79, pp. 319 (1977) no month available.

*Primary Examiner*—Bruce F. Bell
*Attorney, Agent, or Firm*—Birch, Stewart, Kolasch & Birch, LLP

[57] ABSTRACT

There is provided a sensor for the measurement of a content of a material in liquid which material is oxidized with an oxidase enzyme in which sensor a reagent layer is formed on an electrode system composed of a measuring electrode and a counter electrode both of which are formed on an insulating substrate, the reagent layer is composed of a hydrophilic polymer layer comprising a hydrophilic polymer and a reactive layer comprising the oxidase enzyme and an electron carrier, and the reagent layer further comprises a phosphate.

13 Claims, 2 Drawing Sheets

SENSOR AND PRODUCTION METHOD OF AND MEASUREMENT METHOD USING THE SAME

BACKGROUND OF THE INVENTION

1. Field of the Invention

The present invention relates to a sensor which precisely, rapidly and easily measures a concentration of a certain component (for example lactic acid, glucose, cholesterol and so on) in an extremely small amount of liquid such as body fluid (for example blood (whole blood), plasma, urine and saliva), for example a lactic acid sensor, and a method for the production of the sensor and a method for the measurement of the concentration of the certain component in the liquid.

2. Description of the Related Art

Japanese Patent Kokoku Publication (JP-B) No. 58-4557 (1983) discloses a composition for the measurement of lactic acid applied to test paper which measures a lactic acid concentration in blood. In the test paper, a support has a reagent layer thereon which contains lactic acid oxidase (LOD), peroxidase and a color producing reagent. When the paper is used, the lactic acid concentration is determined measuring reflectance which changes based on the lactic acid concentration. Japanese Patent Kokoku Publication (JP-B) No. 5-79319 (1993) proposes a composition for the reagent layer which composition contains lactic acid dehydrogenase, nicotinamide adenine dinucleotide (NADH), an electron carrier and a tetrazolium salt.

In each of those Publications, a coloring reaction is detected using an optical apparatus after blood has been impregnated through a developing layer on the support followed by absorption with the reagent layer. Since a hydrophilic porous members are used for the developing layer and the reagent layer, a relatively large amount of blood (about 20 µl) is required even in the simple measurement method. In addition, when an amount of blood is too small, color producing is not uniform, which may lead to an adverse effect on measurement accuracy or which may make the measurement impossible.

Japanese Patent Kokai Publication (JP-A) No. 6-94672 (1994) discloses a method of quantifying a lactic acid concentration with the use of an enzyme electrode. In the method, a sensor is used which comprises an reagent layer composed of a hydrophilic polymer, LOD, an electron carrier on a measuring electrode and a counter electrode which are both formed on an insulation substrate, and a spacer and a cover are laminated on the reagent layer. Since the electrode of the sensor is small, it can measure even at very small amount of liquid (for example 5 µl). Further, blood is automatically absorbed with capillarity so that the blood spreads uniformly on the electrodes. So, occurrence of mis-measurement is suppressed.

A principle of the measurement with the enzyme electrode using the electron carrier as described above will be explained with an example of the measurement of the lactic acid concentration:

When a substrate "S" (of which concentration is to be measured, for example lactic acid) is oxidized to a product "P" (for example pyruvic acid) by an enzyme "E" (for example lactic acid oxidase), an active center of the enzyme "E" is converted from an oxidizing type "E(ox)" to a reducing type "E(red)". The reducing type enzyme "E(red)" is returned to "E(ox)" through a compound of an oxidizing type "M(ox)" which functions as an electron carrier for the enzyme and the electron carrier is converted to "M(red)". Simultaneously, "M(red)" is electrolyzed to "M(ox)" under a proper applied voltage on a working electrode. A substrate concentration can be determined by measuring oxidizing current upon the electrolysis.

The above measurement principle can be expressed as follows with reference to the lactic acid concentration measurement using lactic acid oxidase (LOD):

Lactic acid + LOD(ox) → pyruvic acid + LOD(red)  (1)
LOD(red) + M(ox) → LOD(ox) + M(red) + H⁺  (2)
M(red) → M(ox) + e⁻  (3)

The measurement method using the enzyme electrode is described in J. R. Mor and R. Guanaccia, Anal. Biochem., vol. 79, pp 319 (1977), which is herein incorporated with the reference.

When such a sensor is used, a liquid sample of, for example, whole blood, plasma, urine or saliva is automatically absorbed under the capillarity by contacting it with a sample inlet of the sensor. As the absorption proceeds, air is vented through an exhaust port so that the liquid sample is distributed throughout the reagent layer. Immediately after the sample absorption has been completed, dissolution of the reagent layer begins and the enzyme reaction proceeds according to the above equation (1).

As the electron carrier, a ferrocene, potassium ferricyanide, a benzoquinone and so are used. The reducing type compound "M(red)" formed in the above equation (2) is electrolytically oxidized according to the above equation (3) by the application of a constant voltage in the range of 0.3 to 0.6 V to the electrode system through an application circuit from an outside power source. Since the current (e⁻) obtained thereon is directly proportional to the lactic acid concentration, the lactic acid concentration in the sample can be obtained by the measurement of the current.

The above sensor almost directly uses what is disclosed in Japanese Patent Kokai Publication (JP-A) No. 3-54447 (1991) with respect to a glucose sensor, and it has a problem peculiar to the enzyme electrode and another problem during the measurement of the lactic acid concentration.

First, an interaction between impurities contained the hydrophilic polymer and the oxidase enzyme increases background current during the measurement. For example, the lactic acid concentration is about one tenth of a glucose concentration in blood. So, if the background current is increased, measurement accuracy is affected especially when the lactic acid concentration is small.

Further, a production cost of the sensor for the concentration measurement of lactic acid is in particular a problem. That is, since LOD is about hundred times as expensive as glucose per a unit, a large amount of LOD is to be contained in the sensor in order for one sensor to cover a large measurable range, which leads to a large cost of the sensor. Thus, an amount of LOD used for the sensor should be minimized from a viewpoint of the production cost.

On the other hand, there is some possibility that the reagent layer is partially peeled off due to dryness of the layer. If the used amount of the LOD is minimized considering the cost, the amount of LOD is insufficient, which makes measurement reproducibility worse.

When other oxidase enzyme is used, similar problems occur which are not so remarkable as in LOD.

Further, when the sensor is stored under a high humidity condition for the purpose of the suppression of the reagent layer dryness, peeling off is prevented. However, the background current is gradually increased due to an effect of remaining water in the reagent layer, which leads to another problem of a worse storage stability of the sensor. Therefore, the reagent layer having a peeling off resistance should be formed immediately after the removal of water content in the reagent layer.

SUMMARY OF THE INVENTION

It is, therefore, an object of the present invention to provide a sensor which precisely measures a content (for example a concentration) of a material to be measured in a liquid sample and which can be produced at a lower cost.

The present invention provides the following modifications (1) to (3) in a reagent layer of a sensor (for example a lactic acid sensor) for the measurement of a content (for example a concentration) of a material to be measured (for example lactic acid) in liquid (for example in blood) which is oxidized by an enzyme in which the reagent layer is formed on at least a portion of an electrode consisting essentially of a measuring electrode and a counter electrode both of which are formed on an insulation substrate, the reagent layer is composed of a hydrophilic polymer layer and a reactive layer comprising an oxidase enzyme, and the reagent layer is preferably is composed of the reactive layer which is formed on the hydrophilic layer:

(1) Addition of a phosphate to the reactive layer increases an activity of the oxidase enzyme so that even a small amount of the oxidase enzyme is not insufficient in its activity and linearity of the activity is obtained up to a high concentration of the material to be measured (for example lactic acid);

(2) Using a highly pure hydrophilic polymer (which is obtained by for example reducing an amount of impurities contained in the hydrophilic polymer by additionally purifying a commercially available hydrophilic polymer) decreases background current so that measurement accuracy is improved; and (3) Further addition of an alkylene oxide polymer to the reactive layer and/or the hydrophilic polymer layer prevents peeling off of the reagent layer.

Therefore, in the first aspect, the present invention provides a sensor (for example a lactic acid sensor) for the measurement of a content (in particular a concentration) of a material in liquid which is oxidized with an oxidase enzyme in which a reagent layer is formed on an electrode system composed of a measuring electrode and a counter electrode both of which are formed on an insulating substrate, the reagent layer is composed of a hydrophilic polymer layer comprising a hydrophilic polymer and a reactive layer comprising the oxidase enzyme (for example lactic acid oxidase, LOD) and an electron carrier, and the reagent layer further comprises a phosphate.

DETAILED DESCRIPTION OF THE INVENTION

Figure 1:
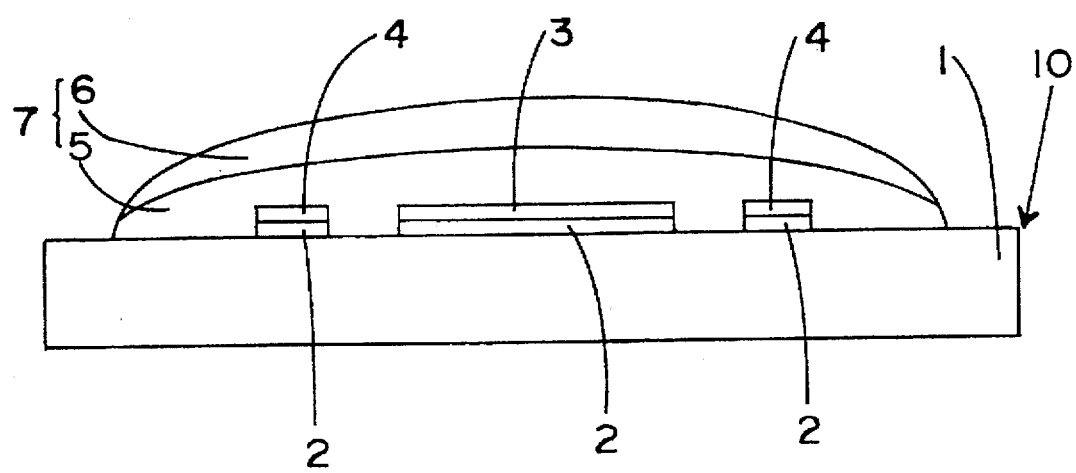
FIG. 1 schematically shows a cross sectional view of the lactic acid sensor of the present invention.

In the present invention, the reagent layer is generally composed of two layers (the hydrophilic polymer layer and the reactive layer). However, these layer are not necessarily separated into to layers in their strict meanings. Optionally, the two layers may be mixed together. Particularly, they may be present together depending on the production method of the sensor.

In the present invention, the measuring electrode is intended to mean an electrode on which the electron carrier is oxidized or reduced, namely an electrode which works for the content measurement of the material to be measured, and the counter electrode means an electrode which is opposed to the measuring electrode.

In the present invention, the oxidase enzyme is an enzyme which catalyzes a reaction oxidizing a biomaterial (i.e. a material in an organism), and includes an oxidase, dehydrogenase and oxigenase and so on. Concretely, lactic acid oxidase, glucose oxidase, cholesterol oxidase, uricase, alcohol oxidase, NADH oxidase, diaphorase, lactic acid dehydrogenase and the like can be exemplified. Also, in the present invention, the material which is oxidized by the oxidase enzyme is a material of which content (such as concentration) is to be measured, namely a measured material. The measured material is lactic acid in the case of lactic acid oxidase, glucose in the case of glucose oxidase, and cholesterol in the case of cholesterol oxidase.

In the present invention, the measured material may be dissolved and/or dispersed in liquid. Further, the liquid is not particularly limited provided that the measured material is dissolved and/or dispersed, and it may be water, ethyl alcohol or a mixture thereof. Thus, the liquid which contains the measured material may be body fluid such as blood, urine, plasma and saliva.

The sensor, the method for the production of the sensor and the method of measuring the content, particularly the concentration (in the case of a solution) using the sensor according to the present inventions will be, hereinafter, explained by an example in which lactic acid oxidase is used as the oxidase enzyme. Such present inventions are equally applied to other oxidase enzymes such as glucose oxidase and cholesterol oxidase. Concretely, lactic acid oxidase should be replaced with other enzyme, and the measured material (lactic acid) should be replaced with a material which is oxidized by said other enzyme when the present inventions are applied to said other oxidase enzyme.

An electrode material which can be used to form the lactic acid sensor of the present invention may be any material which is generally used for electrodes. Concretely, carbon, a metal, an alloy, various compounds of the metal and the alloy (for example an oxide, a hydroxide, a halide, a sulfide, a nitride, a carbide and so on) can be exemplified. In addition, any combination such as a mixture or a composite of those electrode materials may be used.

In the present invention, the mixture means a material in which the electrode materials are mixed together in a micro-order, and the composite means a material in which the electrode materials are mixed together in a relatively larger order than the micro-order (mixed in a so-called macro-order and not so uniformly mixed as the mixture) or a material in which separate materials are combined.

As a preferred metal, silver, aluminum, gold, cobalt, barium, iron, manganese, nickel, lead, zinc, platinum, lithium, copper and so on may be exemplified.

As a preferred alloy, cupro-nickel, manganin, an aluminum-silicon alloy, nickel-copper alloy and so on may be exemplified.

As a particularly preferred metal compound, $MnO_2$, $Ag_2O$, $PbO_2$, $V_2O_5$, AgCl and so on may be exemplified.

When carbon is used, various carbon materials may be used such as graphite, pyrolytic carbon, glassy carbon, acetylene black and carbon black. Of course, conventional amorphous carbon material can be used.

When the electrode materials are used as the mixture or the composite, a combination of $MnO_2$ and acetylene black, a combination of platinum and graphite and a combination of silver and silver chloride can be exemplified.

In the lactic acid sensor according to the present invention, an electrode structure is not particularly limited and various structures can be employed which have been used for the enzyme electrode in the glucose measurement field. The electrode may be in the form of a wire, a rod or a lamina. The electrodes are so arranged that they are connected to a proper circuit which measures current. In a particularly preferred embodiment of the present invention, an electrode in the form of a thin layer is used (see for example FIG. 1).

Such an electrode can be formed by the conventional method for the formation of a laminar electrode. That is, an electrode material paste is prepared by mixing electrode material powder having a predetermined size, a binder (such as a polyvinyl chloride, an epoxy resin, neoprene or cellulose) and a proper solvent (such as tetrahydrofuran, toluene or iso-propanol) and an optional conductive material (such as carbon powder or a conductive polymer); locating the paste on a substrate (such as a poly(ethylene terephthalate) or ceramic strip substrate) in a predetermined thickness (for example within 10 to 200 μm) by a proper method (such as the screen printing); and then drying the paste and preferably sintering the paste to have a laminar electrode having a thickness of 1 to 50 μm.

Further, when necessary, the electrode may be formed in an overlapping form of a plurality of the laminar layers (for example, in a double laminar layer structure). Optionally, a conductive paste such as a silver paste may beforehand be applied to the substrate as a lead by the similar method to that for the formation of the electrode, and then the electrode may be formed on the lead as described above. When the lead is thus formed between the electrode and the substrate, the following effect can be provided: Current is likely to pass the lead of a less resistance so that electrical resistance is reduced, which makes an applied voltage loss reduced.

In the present lactic acid sensor, the reagent layer is formed on at least a portion of each electrode as described above, preferably a whole of each electrode as described above so as to completely cover the electrode. More preferably, a single reagent layer is provided on the both of the electrodes so as to completely cover the electrodes. The reagent layer is composed of the hydrophilic polymer layer and the reactive layer, and any layer may be in contact with the electrodes. Alternatively, each layer is not separated by a clear boundary and one layer is mixed with the other layer in the boundary, or both are mixed together throughout the whole reagent layer. In a particularly preferred embodiment, the hydrophilic polymer layer is formed on the electrode followed by the reactive layer thereon.

The hydrophilic polymer layer functions as a binder which keeps the compounds contained in the reagent layer on the electrode when the sensor is stored. The hydrophilic polymer layer is a thin layer which functions as a separator between the electrode and the reactive layer (when the hydrophilic polymer layer is located between the electrode and the reactive layer), and makes absorption of a sample (such as blood) smooth. The hydrophilic polymer layer comprises a hydrophilic polymer. In the present invention, the hydrophilic polymer is a water-soluble material of a high molecular weight in which a monomer having a hydrophilic group(s) has been polymerized.

The hydrophilic polymer is not particularly limited, but carboxymethyl cellulose (CMC) is preferably used, and other similar polymers may be used. For example, hydroxypropyl cellulose, methyl cellulose, ethyl cellulose may be used. Further, poly(vinyl pyrrolidone) and poly(vinyl alcohol) may be used. Optionally, the hydrophilic layer may further contain a material having a surface activity such as phosphatidylcholine. The hydrophilic polymer layer is applied so as to cover at least a portion of each of the measuring electrode and the counter electrode, and preferably to completely cover the both electrodes. The application may be carried out by coating the electrodes with an aqueous solution of the hydrophilic polymer followed by drying. The hydrophilic polymer layer may have a thickness in the range of for example about 10 to 100 μm.

In the present lactic acid sensor, the hydrophilic polymer is preferably of a high purity, and for example a purity of 99.9% by weight or more is preferable. When no high purity polymer is available, the polymer may be preferably purified by mixing an aqueous solution of the hydrophilic polymer with an organic solvent having a large volatility (such as acetone, tetrahydrofuran, methyl alcohol and so on) into which the hydrophilic polymer is not substantially dissolved so that impurities which is soluble into the organic solvent are removed from the polymer and by drying the recrystallized water-soluble polymer (i.e. the hydrophilic polymer).

Commercially available hydrophilic polymer, for example CMC, has a purity of less than 99.9% by weight (the impurities are redox compounds, dusts in air, various germs, fats and oils and so on), and such CMC is preferably purified to have a purity of not less than 99.9% by weight and more preferably 99.99% by weight so as to use in the present invention. For example, CELLOGEN (commercially available from Dai-ichi Kogyo Seiyaku Co., Ltd.) includes at least 0.1% by weight of redox compounds upon the synthesis of CMC and various germs, dusts and oils as the impurities during the subsequent production process.

In the present invention, when thus highly purified hydrophilic polymer is used, background current is reduced which leads to improved accuracy of the measurement.

In the present lactic acid sensor, the reactive layer constituting the reagent layer comprises lactic acid oxidase (LOD), the electron carrier and the phosphate which are uniformly mixed together in a solid phase, preferably in a thin solid layer covering at least portions the measuring electrode and the counter electrode. Thus, when the hydrophilic polymer is present as a separate layer, the reactive layer is present on at least a portion of the hydrophilic polymer layer.

Such thin layers (the hydrophilic polymer layer and the reactive layer) may be formed by methods which are similar to the method for the formation of the electrode as described above. For example, a reagent paste is prepared which comprises the enzyme, the electron carrier, the binder and the solvent (for example water or ethanol, preferably ethanol), the paste is placed on the electrodes by a proper method (for example using a dispenser) so as to cover the electrodes and then the paste is dried into the solid phase.

In the present lactic acid sensor, any electron carrier may be used which has been conventionally used for the so-called enzyme electrode. For example, potassium ferricyanide, benzoquinone, phenazine methosulfate, thionine, ferrocene, naphthoquinone, Methylene Blue, methoxy PMS, Meldola's Blue and so on can be used.

The phosphate in the reactive layer used in the present lactic acid sensor is a salt which is dissolved into water to be ionized and to provide an alkaline solution. For example, dipotassium hydrogenphosphate is preferably used, to which the phosphate is not limited. As other phosphates, the following can be exemplified: potassium dihydrogenphosphate, disodium hydrogenphosphate, sodium dihydrogenphosphate, calcium phosphate and magnesium phosphate. These phosphates promote LOD's activity to improve the measurement accuracy.

Further, the reactive layer of the present lactic acid sensor preferably includes a polymer in which ester bonds are mainly present, in particular an alkylene oxide polymer. For example, the polymer is an alkylene oxide addition polymer which is esterified and/or transesterified with a polycarboxylic acid and/or its derivative to have a molecular weight of about 20000 to 300000. Inclusion of such a polymer provides the lactic acid sensor having improved reproducibility. As the alkylene oxide, the following may be used: ethylene oxide, propylene oxide, styrene oxide and butylene oxide. As the polycarboxylic acid and its derivative, the following may be used: malonic acid, succinic acid, maleic acid, fumaric acid, phthalic acid, tetrabenzyl carboxylic acid and an anhydride such as succinic anhydride and maleic anhydride, a lower alkyl ester such as dimethyl phthalate and dimethyl maleate.

As the alkylene oxide polymer used in the present invention, a polymer can be used which has a plasticizer property and a rapid dissolution rate into water. For example, an ethylene oxide polymer or a propylene oxide polymer may be used. Such a polymer is for example commercially available as PAOGEN PP-15 or PAOGEN EP-15 from Dai-ichi Kogyo Seiyaku Co., Ltd.

Those alkylene oxide polymers contribute to peeling off prevention of the reagent layer, which results in ensuring the measurable range by the sensor.

In the present invention, any suitable combination of the electrode material, the electron carrier, the phosphate and the hydrophilic polymer and the optional alkylene oxide polymer can be employed. The above modification (1), (2) or (3) may be employed alone or in any combination thereof.

Matters to be considered in the present invention are a lactic acid concentration range to be measured, a reduction potential or an oxidation potential of the electron carrier, an electromotive force generated by the combination of the electrodes, a production cost, stabilities, a composition of the reaction layer and so on. Depending on the combination of those matters, a suitable lactic acid sensor having proper features can be produced using for example the try and error method.

One concrete example of a preferred sensor is shown below:

| | |
|---|---|
| Insulation substrate material: | polyethylene terephthalate |
| Electrode material: | graphite |
| Hydrophilic polymer layer material: | CMC (purified by re-crystallization) |
| Reactive layer material composition | |
| lactic oxidase: | 200–800 units/ml. |
| electron carrier: | potassium ferricyanide 1.0 to 5.0% by weight |
| phosphate: | dipotassium hydrogenphosphate 0.01 to 1.00% by weight |
| alkylene oxide polymer: | PAOGEN 0.01 to 1.00% by weight |

The lactic acid sensor according to the present invention may comprise a spacer and a cover which are used in the conventional enzyme electrode on the reactive layer in the solid phase which comprises LOD, the electron carrier and the phosphate.

FIG. 1 schematically shows a cross sectional view of the lactic acid sensor of the present invention. In FIG. 1, the lactic acid sensor 10 comprises an insulation substrate 1 on which leads 2 is located. Electrodes (a measuring electrode 3 and a counter electrode 4) are formed on the leads 2. In the embodiment shown in FIG. 1, a reagent layer 7 composed of a hydrophilic polymer layer 5 and a reactive layer thereon is located on the electrodes so that it completely cover them. As described above, the reagent layer preferably covers the whole of the electrodes. However, it is not necessarily so and it is sufficient to cover at least a portion of each electrode.

In the second aspect, the present invention provides a method for the production of the sensor (for example the lactic acid sensor) of the first aspect.

That is, the method comprises the steps of:

forming an electrode system composed of a measuring electrode and a counter electrode on an insulating substrate;

coating at least a portion of the electrode system with a hydrophilic polymer layer by applying a solution, preferably an aqueous solution containing a hydrophilic polymer to the electrode system followed by drying; and coating at least a portion of the hydrophilic polymer layer with a reactive layer by applying a solution, preferably an aqueous solution containing a composition for the reactive layer comprising an oxidase enzyme (for example lactic acid oxidase), an electron carrier and a phosphate to the hydrophilic polymer layer followed by drying.

When the hydrophilic polymer layer and the reactive layer are formed, the solutions (for example the aqueous solutions) for the those layers are prepared, and the solutions are applied (for example dispensed) to the electrode system followed by drying thereof to remove the solvents.

In the production method, when the solution for the reactive layer is prepared so as to have a phosphate concentration of 0.01 to 1.00% by weight, particularly 0.10 to 0.50% by weight, the sensor (lactic acid sensor) can be produced which has a particularly better reproducibility and sensitivity.

When the alkylene oxide polymer is contained in the hydrophilic layer and/or the reactive layer, the solution for the formation of each layer preferably contains the polymer of 0.01 to 1.00% by weight, particularly 0.10 to 0.50% by weight, which is effective for the formation of the peeling off resistant reagent layer.

In addition, the thus formed reagent layer may have thereon the spacer and the cover used in the conventional enzyme electrode, which have an aperture(s) through which a sample supplied on the cover can pass and penetrate toward the reactive layer and the electrode system.

The matters which have been explained in the above with regard to the sensor of the present invention (lactic acid sensor) are also applied to the production method of the sensor (lactic acid sensor) and a measuring apparatus and a measuring method of the present invention which will be described below when they are proper.

In the third aspect, the present invention provides a measuring apparatus for the concentration measurement of a material (for example lactic acid) which is oxidized by an enzyme in liquid with using the present sensor (lactic acid sensor) described in the above. That is, the apparatus comprises a sample supply detection circuit, a measurement timing control circuit, an arithmetic circuit, a displaying circuit and a display member which indicate the concentration display, and it further comprises a member which receives or hold the sensor of the present invention (for example lactic acid sensor) so that the measurement timing control circuit can detect current generated in the sensor (for example lactic acid sensor) depending on the concentration of the material to be measured.

In the present invention, the sample supply detection circuit is a circuit which detects an impedance change due to penetration of the sample from a sample absorbing inlet which is through the cover and the spacer on the reagent layer of the sensor (for example lactic acid sensor) and starts a measurement program automatically.

In the present invention, the measurement timing control circuit is a circuit which measures the current when an enzyme reaction proceeds after the supply of the sample and a circuit is closed after a period sufficient for the production of a product "P".

In the present invention, the arithmetic circuit is a circuit which converts the current value detected by the measurement timing control circuit into a concentration of the material to be measured (for example lactic acid) based on an arithmetic equation (or a calibration curve) which has been beforehand installed in the apparatus.

In the present invention, the display circuit is a circuit which show the concentration converted by the arithmetic circuit on the display member of the apparatus.

As the above circuits described above, those may be used which are used in the apparatus including the conventional enzyme electrode. Detailed circuit information thereon can be obtained from for example Japanese Patent Kokai (JP-A) No. 4-357452 (1992), and the contents thereof are incorporated herein by the reference.

In the forth aspect, the present invention provides a method for the measurement of a concentration of a material (lactic acid) to be measured with using the sensor (for example lactic sensor) in the measurement apparatus (namely with being held by the sensor receiving member). The concentration of the material to be measured (for example lactic acid) by the present invention is not specifically limited and it may depend on an amount of the sample to be used for the measurement. Also, the amount of the sample used for the measurement is not specifically limited. For example, an amount of 1.0 to 5.0 µl, particularly 3.0 to 5.0 µl may be used for the measurement. When such an amount is employed, the present method is particularly effective of the measurement of the measured material concentration in the range of for example 0 to 200 mg/dl, in particular 2 to 100 mg/dl.

According to the present sensor, the following major effects are obtained:

(1) The inclusion of the phosphate by the reactive layer suppresses the degradation of the oxidase enzyme (for example LOD) activity so that the concentration measurement is possible even though the measured material is present in a higher concentration. So, the concentration measurement is possible even with a small amount of oxidase exzyme, which reduces the production cost of the sensor (for example lactic acid sensor);

(2) The use of the purified hydrophilic polymer for the polymer layer reduces the background current so that the measurement accuracy of the sensor (for example lactic acid sensor) is improved; and (3) The inclusion of the alkylene oxide polymer by the hydrophilic polymer layer and/or the reagent layer prevents the reagent layer from peeling off so that the measurement reproducibility is improved.

Thus, the sensor (lactic acid sensor) having the improved accuracy, sensitivity and reproducibility is provided under those effects.

EXAMPLES

Examples of the present invention will be explained hereinafter in detail. In the Examples, the method for the production of the lactic acid sensor is also explained as an example. However, the present invention is not limited to the lactic acid sensor, and when glucose oxidase is used as the enzyme, a glucose sensor is obtained similarly. When cholesterol oxidase is used, a cholesterol sensor is obtained similarly.

Example 1

Leads 2 were printed on an insulation substrate 1 of polyethylene terephthalate using silver paste with the screen printing, and a measuring electrode 3 and a counter electrode 4 were printed on the leads 2 using conductive carbon paste.

Then, an aqueous solution of 0.5% by weight of CMC as the hydrophilic polymer (commercially available from Dai-ichi Kogyo Seiyaku Co., Ltd. as a trade name of CELLOGEN) was dispensed on the electrodes followed by drying to form a hydrophilic polymer layer 5. Subsequently, a solution having the following composition was dispensed on the polymer layer followed by drying to form a reactive layer 6. Thus formed lactic acid sensor is schematically shown in FIG. 1 in its cross sectional view.

| LOD | 400 U/ml |
|---|---|
| potassium ferricyanide | 2.0% by weight |
| dipotassium hydrogenphosphate | 0.5% by weight |

Comparative Example 1

A prior art sensor was formed by repeating Example 1 except that the solution for the reactive layer was prepared without addition of dipotassium hydrogenphosphate. Thus, the solution had the following composition:

| LOD | 400 U/ml |
|---|---|
| potassium ferricyanide | 2.0% by weight |

Comparative Example 2

A prior art sensor was formed by repeating Example 1 except that the solution for the reactive layer was prepared without addition of dipotassium hydrogenphosphate. Also, it should be noted that the solution had the following composition:

| LOD | 800 U/ml |
|---|---|
| potassium ferricyanide | 2.0% by weight |

Figure 2:
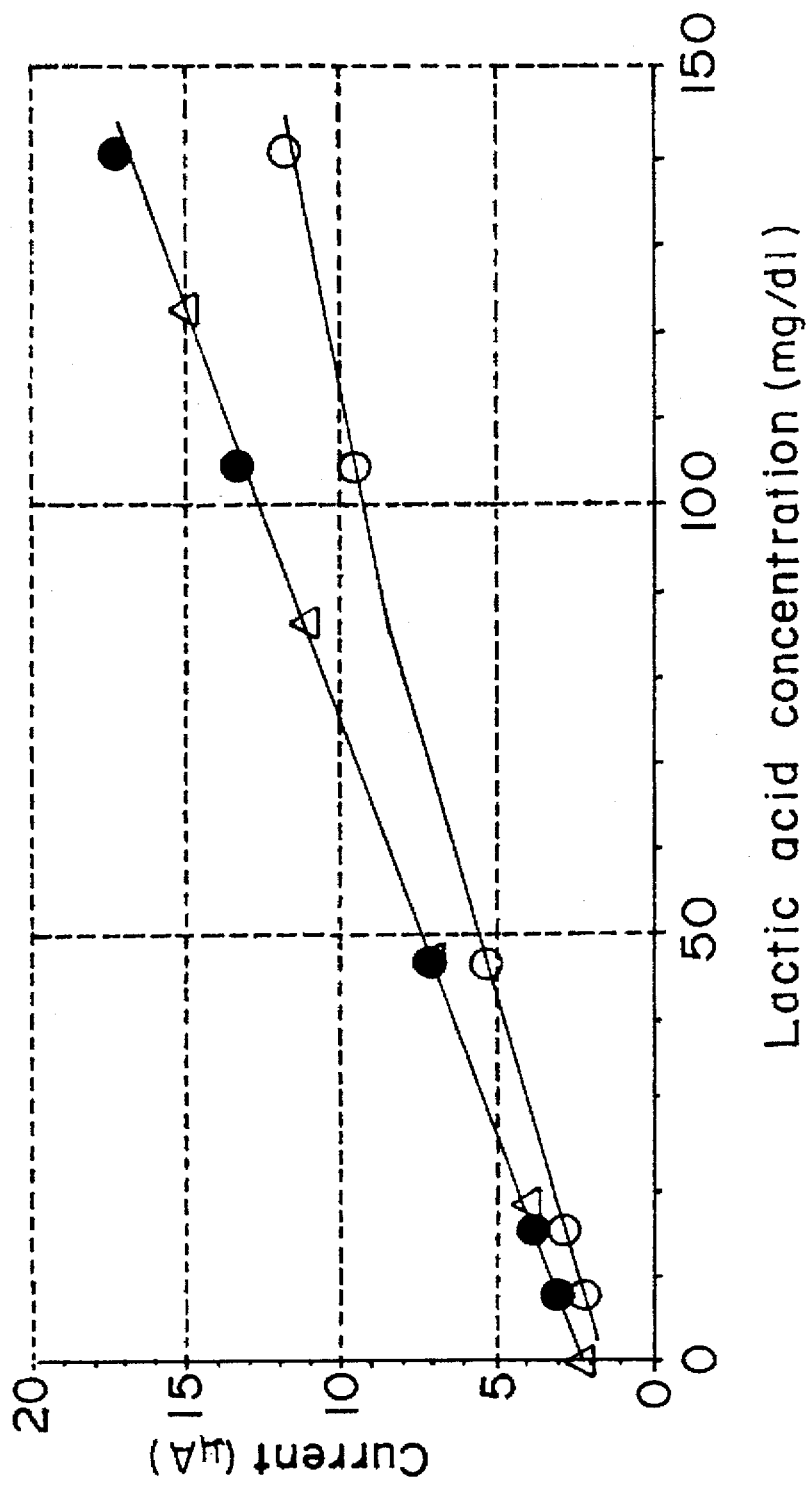
FIG. 2 is a graph which shows a response curve of a sensor produced in Example 1 with respect to a lactic acid concentration.

Lactic acid concentration in blood was measured using the sensors produced in Example 1 and Comparative Examples 1 and 2. The results thereof are shown in FIG. 2 by plotting current values generated through the reaction against the lactic acid concentrations in the blood. Upon the measurement, about 5 µl of blood was used. As seen from FIG. 2, when dipotassium hydrogenphosphate was added, a linear relationship similar to that of the prior art sensor is obtained even though an amount of the enzyme is reduced by 50% relative to the prior art sensor. That is, no sensitivity is adversely affected even though the amount of the enzyme is reduced, so that a cheaper lactic acid sensor can be provided which has the same performance as in the prior art sensor.

Example 2

Example 1 was repeated except that purified CMC was used. CMC (commercially available as CELLOGEN) was purified in the following manner:

First, one gram of CMC was dissolved into 100 ml of water. Then, 300 ml of acetone was gradually added to the water while stirring with a glass rod. Immediately, white fibrous CMC precipitated and it was taken out using the glass rod. The CMC was dried at 50° C. for 60 minutes.

Thus produced lactic acid sensor was used for the measurement of the lactic acid concentration in blood and CV (coefficient of variation) values of the measurements (index of reproducibility; a larger CV value means worse reproducibility) are shown below:

| Lactic acid concentration (mg/dl) | CV (%) |
| --- | --- |
| 9.4 | 6.2 |
| 18.6 | 2.6 |
| 53.2 | 1.6 |
| 101.2 | 0.9 |

Comparative Example 3

Example 2 was repeated except that commercially available CMC was used without purification and the lactic acid concentration in blood was measured. The results are shown below:

| Lactic acid concentration (mg/dl) | CV (%) |
| --- | --- |
| 9.4 | 12.6 |
| 18.6 | 4.9 |
| 53.2 | 2.3 |
| 101.2 | 1.4 |

When the results of Example 2 are compared with those of Comparative Example 3, it is seen that the purification of CMC improves the reproducibility, so that the lactic acid sensor having the better accuracy is provided.

Example 3

Example 1 was repeated except that the solution for the reactive layer further comprised 0.25% by weight of PAOGEN (trademark, commercially available from Dai-ichi Kogyo Seiyaku Co., Ltd.) as the alkylene oxide polymer.

Thus produced lactic acid sensor was used for the measurement of the lactic acid concentration in blood and CV values of the measurements are shown below:

| Lactic acid concentration (mg/dl) | CV (%) |
| --- | --- |
| 9.4 | 5.9 |
| 18.6 | 1.6 |
| 53.2 | 1.4 |
| 155.4 | 2.3 |

Comparative Example 4

Example 3 was repeated to produce the lactic acid sensor except that PAOGEN was not used and the lactic acid concentration in blood was measured similarly using the sensor. The results are shown below:

| Lactic acid concentration (mg/dl) | CV (%) |
| --- | --- |
| 9.4 | 10.4 |
| 18.6 | 2.6 |
| 53.2 | 2.7 |
| 155.4 | 2.4 |

It is seen from the above results that the addition of PAOGEN improves the CV values, especially in the lower lactic acid concentration range. It is contemplated that the improvement would be due to the peeling off prevention effect of PAOGEN.

What is claimed is:

1. A sensor for the measurement of a content of a material in liquid which material is oxidized with an oxidase enzyme in which sensor a reagent layer is formed on an electrode system composed of a measuring electrode and a counter electrode both of which are formed on an insulating substrate, and the reagent layer is composed of a hydrophilic polymer layer comprising a hydrophilic polymer and a reactive layer comprising the oxidase enzyme and an electron carrier wherein the reactive layer further comprises a phosphate.

2. The sensor according to claim 1 wherein the oxidase enzyme is lactic acid oxidase and the sensor is used for the measurement of a lactic acid concentration in the liquid.

3. The sensor according to claim 1 wherein the hydrophilic polymer is purified to at least 99.9% by weight.

4. A sensor for the measurement of a content of a material in liquid which material is oxidized with an oxidase enzyme in which sensor a reagent layer is formed on an electrode system composed of a measuring electrode and a counter electrode both of which are formed on an insulating substrate, and the reagent layer is composed of a hydrophilic polymer layer comprising a hydrophilic polymer and a reactive layer comprising the oxidase enzyme and an electron carrier wherein the reactive layer further comprises a phosphate, wherein at least one of the hydrophilic polymer layer and the reactive layer further comprises an alkylene oxide polymer.

5. A method for the production of a sensor comprising the steps of:

forming an electrode system composed of a measuring electrode and a counter electrode on an insulating substrate;

coating at least a portion of the electrode system with a hydrophilic polymer layer by applying a solution containing a hydrophilic polymer to the electrode system followed by drying the solution; and coating at least a portion of the hydrophilic polymer layer with a reactive layer by applying a solution containing a composition for the reactive layer comprising an oxidase enzyme, an electron carrier and a phosphate to the hydrophilic polymer layer followed by drying the solution.

6. The method for the production of the sensor according to claim 5 wherein the oxidase enzyme is lactic acid oxidase and the sensor is used for the measurement of a lactic acid concentration in the liquid.

7. The method for the production of the sensor according to claim 5 wherein the hydrophilic polymer is purified to at least 99.9% by weight.

8. The method for the production of the sensor according to claim 5 wherein the solution containing a composition for the reactive layer includes 0.01 to 1.00% by weight of the phosphate.

9. A method for the production of a sensor comprising the steps of:

forming an electrode system composed of a measuring electrode and a counter electrode on an insulating substrate;

coating at least a portion of the electrode system with a hydrophilic polymer layer by applying a solution containing a hydrophilic polymer to the electrode system followed by drying the solution; and coating at least a portion of the hydrophilic polymer layer with a reactive layer by applying a solution containing a composition for the reactive layer comprising an oxidase enzyme, an electron carrier and a phosphate to the hydrophilic polymer layer followed by drying the solution, wherein at least one of the solution containing the hydrophilic polymer and the solution containing a composition for the reactive layer includes an alkylene oxide polymer.

10. The method for the production of the sensor according to claim 9 wherein a concentration of the alkylene oxide polymer in the solution is in the range of 0.01 to 1.00% by weight.

11. A method for measuring the concentration of lactic acid in a sample comprising:

contacting a sample with a sensor in which a reagent layer is formed on an electrode system composed of a measuring electrode and a counter electrode both of which are formed on an insulating substrate, the reagent layer is composed of a hydrophilic polymer layer comprising a hydrophilic polymer and a reactive layer comprising lactic acid oxidase and an electron carrier, and the reactive layer further comprises a phosphate;

obtaining a current value; and converting the current value into a concentration of the lactic acid in the sample.

12. A sensor for the measurement of a content of a material in liquid which material is oxidized with an oxidase enzyme in which sensor a reagent layer is formed on an electrode system composed of a measuring electrode and a counter electrode both of which are formed on an insulating substrate, and the reagent layer is composed of a hydrophilic polymer layer comprising a hydrophilic polymer and a reactive layer comprising the oxidase enzyme and an electron carrier wherein the hydrophilic polymer is purified to at least 99.9% by weight.

13. A sensor for the measurement of a content of a material in liquid which material is oxidized with an oxidase enzyme in which sensor a reagent layer is formed on an electrode system composed of a measuring electrode and a counter electrode both of which are formed on an insulating substrate, and the reagent layer is composed of a hydrophilic polymer layer comprising a hydrophilic polymer and a reactive layer comprising the oxidase enzyme and an electron carrier wherein at least one of the hydrophilic polymer layer and the reactive layer further comprises an alkylene oxide polymer.

* * * * *